United States Patent [19] [11] 4,044,607
Deal [45] Aug. 30, 1977

[54] GRAIN MOISTURE MEASUREMENT PROBE

[75] Inventor: Clarence D. Deal, Oklahoma City, Okla.

[73] Assignee: Electromeasures, Inc., Ennis, Tex.

[21] Appl. No.: 682,013

[22] Filed: Apr. 30, 1976

[51] Int. Cl.² ........................... G01R 27/26
[52] U.S. Cl. ..................... 73/73; 324/61 P; 324/61 QS
[58] Field of Search .............. 73/73; 324/61 P, 61 QS

[56] References Cited
U.S. PATENT DOCUMENTS

| 3,046,479 | 7/1962 | Mead et al. | 324/61 QS |
| 3,426,271 | 2/1969 | Alais | 324/61 P |
| 3,681,685 | 8/1972 | Tarry et al. | 324/61 QS |
| 3,794,911 | 2/1974 | Fathauer | 324/61 QS |

OTHER PUBLICATIONS

Motorola–Silicon Zener Diode and Rectifier Handbook, pp. 98-101 (1961).

Primary Examiner—James J. Gill
Assistant Examiner—Anthony V. Ciarlante
Attorney, Agent, or Firm—Bacon & Thomas

[57] ABSTRACT

An apparatus for measuring the moisture content of grain includes a probe having an oscillator circuit therein. The oscillator circuit includes a function generator, temperature sensing means in contact with the grain and a pair of juxtapositioned capacitor electrodes within the probe, but not in contact with the grain. The output of the oscillator circuit is connected to readout means including a phase locked loop, operational amplifier and indicating means.

11 Claims, 3 Drawing Figures

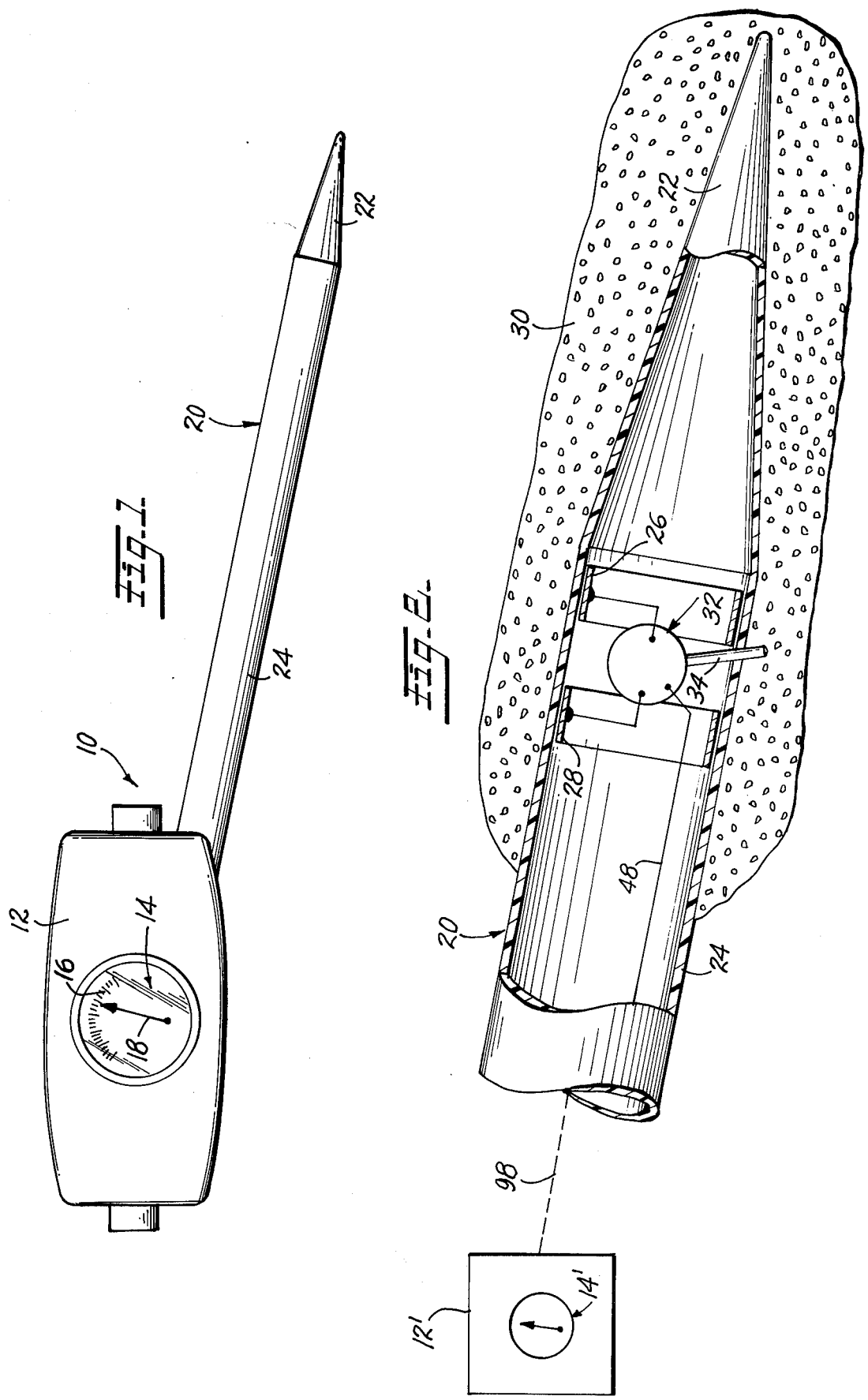

GRAIN MOISTURE MEASUREMENT PROBE

FIELD OF THE INVENTION

The invention relates generally to improvements in grain quality measurements, and more particularly to improvements in grain moisture and/or dielectric constants that are relatively independent of the quantity of the grain sample.

BACKGROUND OF THE INVENTION

Grain should not be stored in granaries or elevators if it is too wet or of poor quality due to excessive dryness. The current state of the art permits only a cursory and sometimes theoretical determination of this parameter, particularly during the busy harvest season. Presently used methods are also time consuming, and the devices are normally not portable.

It is a well known physical phenomenon that the ability to store energy or capacitance of an electrical circuit is directly proportional to the dielectric constant of the material between two conductors. It is also a well known electrical phenomenon that the frequency of an oscillating circuit is determined in part by the capacitance thereof. Therefore, it is quite common to measure the dielectric constant of a material by determining the frequency of oscillation of a circuit when the unknown dielectric is placed between two plates of a capacitor.

The quality of grain and/or its readiness for harvest may be determined in part by its dielectric constant. Current techniques require a rather cumbersome procedure for the measurement of grain quality; therefore, the lay elevator operator and farmer quite often neglect this measurement or obtain inaccurate results.

SUMMARY AND OBJECTS OF THE INVENTION

The present invention contemplates a novel, accurate, easy to use measurement system, adaptable to all types of grain, for determination of grain quality.

A primary object of this invention is to allow accurate measurement of the grain while it is still in the delivery truck, thus obviating prior art techniques that require taking a sample from the truck into an office and laboriously measuring it.

An object of this invention is to provide a novel measurement system for the determination of grain quality that is unaffected by the electrical resistance thereof.

Another object of the invention is to provide a novel measurement system for the determination of grain quality that may be inserted in a bed of grain and thus allow measurements at various levels of the bed.

Another object of the invention is to provide a novel measurement system for the determination of grain quality that is unattached physically to any other device, i.e., a completely portable system.

Another object of the invention is to provide a novel measurement system for the determination of grain quality by the automatic analysis of the grain dielectric constant.

Another object of the invention is to provide a novel measurement system that is sufficiently rapid and easy to make that lay grain elevator operators may initiate accurate measurements of the grain influx.

A further object of the invention is to provide a novel measurement system that is relatively independent of the amount of grain surrounding the measuring electrodes by using juxtapositioned electrodes in lieu of coaxial electrodes.

The moisture measuring unit of the instant invention includes a probe made of plastic material. A pair of capacitive electrodes are placed in juxtaposition along the probe wherein the electrostatic field formed therebetween is a divergent field. The capacitor plates and a temperature compensation diode cooperate with a function generator to provide an output corresponding to the quality of the grain being measured. The output from the function generator is fed either remotely or through a cable to a readout circuit which includes a phase locked loop, an operational amplifier and finally a meter or digital readout to indicate the quality of the grain. There is provided means in the operational amplifier feedback circuit for selecting the type of grain which is to be measured. The unit can be completely portable by use of rechargeable batteries.

BRIEF DESCRIPTION OF THE DRAWINGS

The above and other advantages and objects of the invention will be better appreciated from the following description and claims wherein:

FIG. 1 is a side elevation view of one embodiment of the probe of the instant invention;

FIG. 2 is an enlarged elevation view, partly in section, of the probe element in FIG. 1.

DETAILED DESCRIPTION OF THE INVENTION

Figure 3:
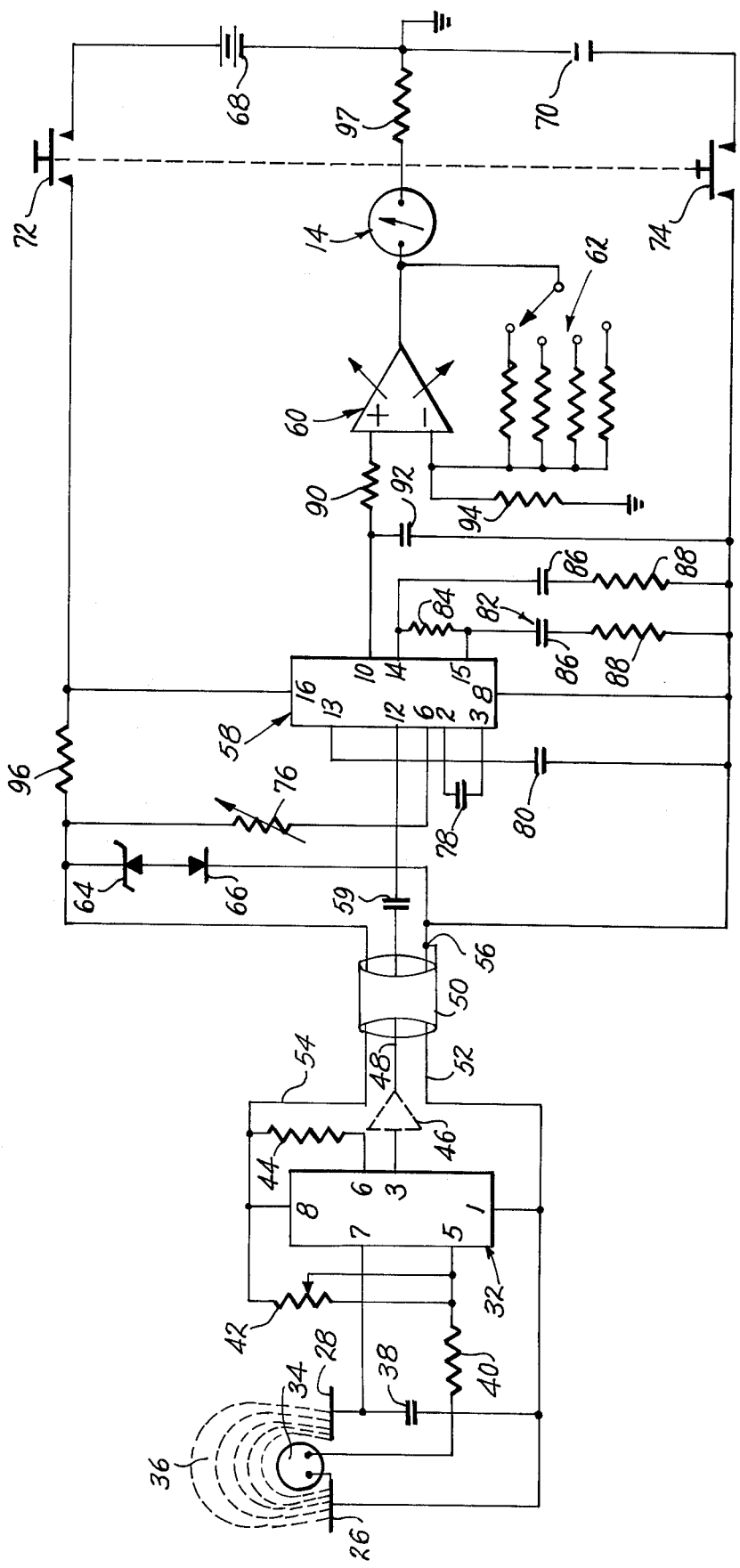
FIG. 3 is a schematic of the circuit involved in the instant invention.

Referring to FIG. 1, a portable moisture detecting unit 10 includes a housing 12 having a meter 14 positioned thereon. The meter includes a dial 16 and a needle 18. As will be appreciated from a discussion of the circuitry below, the particular meter disclosed could be replaced by a digital readout type meter or the like.

Extending outwardly from the housing is a probe 20 of suitable length. The probe 20, as seen in FIG. 2 has a pointed end 22 and a cylindrical portion 24. Mounted near the pointed end 22 are a pair of juxtapositioned capacitor electrodes 26 and 28. They may be flat or may be cylindrical conforming to the shape of the probe casing 24 as shown in FIG. 2. The capacitor electrodes 26 and 28 form a capacitor with the surrounding grain 30 being the varying dielectric therebetween with said capacitor forming a divergent electrostatic field substantially symmetrical about the probe. In order that there is no resistance factor, the probe 20 is formed of plastic or other nonconducting material of a known dielectric. A function generator broadly seen as 32 in FIG. 2 is connected to the capacitor electrodes 26 and 28. A temperature sensing device is diagrammatically seen at 34. The operation of the various elements will be discussed with relation to FIG. 3.

As seen in FIG. 3 the electrodes 26 and 28 forming the capacitor are in juxtaposition so that an electrostatic field 36 is formed therebetween. The electrostatic field 36 is a divergent field rather than a convergent field. The advantage of a divergent field, as opposed to a convergent field, is that when electrodes are coaxial to form a convergent field the amount of material placed between the electrodes is critical. However, in a divergent field the amount of material in each sample being tested is much less critical because it is the grain closest to the capacitor electrodes which have the greatest effect upon the capacitance. The farther out from the electrodes one goes, the less effect on the capacitance there is.

Temperature sensor 34 is placed in the probe such that it is in contact with the grain to be measured because the moisture content, or the quality of the grain, is also dependent upon its temperature. Temperature sensing element 34 is preferably a diode type since it has very linear characteristics with regard to temperature.

Function generator 32 is preferably in the form of a common integrated circuit. As will be seen below, the purpose of the integrated circuit function generator is to generate a voltage, the frequency of which is dependent upon the capacitance between terminal 7 and terminal 1 which is the ground for the device. Function generator 32 also has the ability to modulate or change its frequency with the voltage that is placed on pin number 5 whereby it is a voltage controlled oscillator by varying the voltage on pin 5. The frequency of oscillation is changed by varying the capacitance between pins 7 and 1.

A capacitor 38 is placed across the capacitor electrodes 26 and 28 for the purpose of establishing the frequency when the probe is out of the grain. In other words, when there is no dielectric material adjacent electrodes 26 and 28, there must be a certain amount of capacitance to establish a base frequency.

A plurality of resistors 40, 42 and 44 provide bias for the oscillator circuit. Resistor 40 connected to pin 5 establishes the current through temperature sensing diode 34 so that one obtains proper voltage on pin 5 for temperature compensation. Resistor 42, also connected to pin 5, is seen as a variable resistance so as to have ability to calibrate the temperature compensating circuitry including diode 34.

An amplifier 46 (seen in dotted lines) may be connected in line 48 emanating from pin number 3. This will be discussed below.

The signal from function generator 32 will be a square wave, the frequency of which is dependent upon the dielectric of the material surrounding electrodes 26 and 28, as well as the temperature of the material surrounding the probe.

The probe seen again in FIG. 2 is connected to additional circuitry and readout means seen in box 12'. This may be attached directly to the probe 20 or by remote control as will be discussed below.

Referring again to FIG. 3, the signal is fed through the remainder of probe 20 which may be in the form of a shielded cable 50. The purpose of the shielding is to decrease noise. In addition to line 48, a common line 52 and a third line 54 run through the shielded cable to the remainder of the circuitry in box 12'. The cable 50, if shielded, is attached at 56 to common line 52.

The line 48, is connected through a capacitor 59 to a phase locked loop 58. This is also a conventional integrated circuit which has extremely low power consumption. The capacitor 59 capacity couples the phase locked loop 58 to the output of the function generator 32 so that any DC voltage that is present on the output of function generator 32 is not passed to the phase locked loop whereby the phase locked loop has only an AC voltage at its input.

As will be seen from the discussion below, the phase locked loop has a DC error voltage emanating therefrom which is dependent upon the frequency change. In other words, it provides a DC voltage output that is proportional to the frequency change of the frequency generator-oscillator in the probe. Thus, as the probe is inserted into different materials, the frequency will change, and the DC output of loop 58 will be proportional to the frequency of the oscillator in the probe. The DC voltage is what is ultimately measured on meter 14 as being the characteristic or the quality of the grain.

An operational amplifier 60 is connected to the phase locked loop 58, the gain of the amplifier being adjusted by means of various resistors 62 corresponding to the particular type of grain being measured. The reason for the resistor 62 is that each different grain will have a corresponding effect on the oscillator. Thus, the unit would be calibrated for each type of grain desired to be measured.

Meter 14, as mentioned above, is calibrated to read the quality of the grain because the voltage across the meter is a direct relationship to the dielectric constant of the grain that is in contact with the probe.

A zener diode 64 and a diode 66 in series with zener 64 establish a well regulated DC voltage supply to the function generator 32. Zener 64 normally would be a 10-volt diode. The diode 66 provides temperature compensation for the zener. The entire unit will have good temperature characteristics which is important because of widely varying temperatures, particularly when one considers a prime purpose of the invention is to measure grain. In the sun during late summer, the temperature could be well over 100° F., whereas in the winter it could be below 0° F. Thus, there is a need for very accurate temperature compensation which the pair of diodes provide, whereby the voltage to the function generator remains constant. A pair of batteries 68 and 70 are used to provide better operation for the operational amplifier. While one battery could be used, it has been found that by dividing the 12-volt battery into, for example, two 6-volt batteries there is provided a good reference for the midpoint of the operational amplifier. An advantage of using a 12-volt system is that the unit can be charged from the cigarette lighter of a vehicle.

A pair of ganged switches 72 and 74 are inserted adjacent the batteries. A variable resistor 76 is connected to pin number 6 of the phase locked loop 58. Resistance 76 is adjustable to match the rest or zero frequency of the oscillator circuit in the probe. A capacitor 78 between pins 2 and 3 cooperates with resistance 76 to provide the matching frequency.

A capacitor 80 between pin 13 and common is inserted on the control voltage from the phase locked loop to reduce noise.

Terminals 14 and 15 of the phase locked loop are connected to a low pass filter 82 which includes a high resistance 84, a pair of capacitors 86 and a pair of low ohm resistors 88. These form a low pass filter to feed back into terminal 15 to control the oscillator and the phase locked loop. Terminal 10 of the phase locked loop is the output terminal giving a DC voltage out of the phase locked loop, the DC voltage being proportional to the change in frequency resulting from the change in frequency emanating from the function generator in the probe. Thus, the DC voltage is proportional to the frequency change. A resistor 90 and a capacitor 92 provide another low pass filter at the input of the operational amplifier 60. The negative input to the operational amplifier is connected to a feedback circuit which includes the bank of resistors 62. Also connected to the negative input of the operational amplifier is a low resistance in the form of resistor 94 connected to ground. Thus the gain of the operational amplifier is determined by the ratio of resistors 62 and 94. Thus the ratio of whichever resistor in bank 62 is connected, divided by the resistance of resistor 94 provides the gain of the operational amplifier. In this way, the resistors in bank 62 are used to adjust the gain of the amplifier to provide an appropriate output of each different type of grain.

A resistor 96 in the order of 200 ohms is placed in the battery-zener circuit to permit the proper operation of the zener. For example, the voltage emanating from the batteries will be in the order of 12.6 volts. Assuming that the zener diode 64 is rated at 10 volts, it, together with diode 66, one will have 10.6 volts, then there will be a two volt drop across resistor 96. This resistance is thus required to absorb the variations in load so that the zener 64 can properly regulate the voltage.

A resistor 97 is connected between one terminal of meter 14 and a ground connection between batteries 68 and 70.

As discussed above, the capacitor electrodes 26 and 28 are encapsulated in plastic material so that there is no resistive contact with the grain since there is no interest in measuring the resistance of the grain, only measuring the dielectric. This is a distinct advantage over the prior art use of coaxial electrodes which are bare metal so that when the grain is in contact with the electrodes, the resistance of the grain will affect the reading.

The embodiment seen in FIG. 3, which includes the shielded cable connection 50, is used for direct readout. However, if one were to have a remote readout, for example, having the probe in the grain as it arrives at an elevator in a truck and the readout being inside, amplifier 46 would be connected to output pin 3 of the function generator 32. If the cable is unshielded and line 48 is of sufficient length, there is in effect an antenna. Thus, the unshielded wire 48 will radiate because the frequency emanating is in the order of 300 kHz. Obviously, referring to FIG. 2, the dotted lines 98 would either represent the cable connection or an antenna connection wherein "box" 12' would have its appropriate antenna and amplifier corresponding with amplifier 46 in FIG. 3.

In operation, the probe 20 is inserted into the grain as many times as one wants to sample a particular load of grain, and as deeply as one wants to measure. The bank of resistors 62 is adjusted to conform to the particular grain being measured. The oscillator formed by frequency generator 32, capacitor electrodes 26 and 28, temperature compensating diode 34 and the other elements in the probe generate a frequency dependent upon the capacitance between the electrodes and the temperature of the material being measured. This signal is sent to the phase locked loop 58 and operational amplifier and an output is read on meter 14 or an equivalent digital readout, thus telling the operator the quality of the grain.

It will be appreciated that the unit described can be used as either a hand unit for inserting the probe in a bed of grain in the truck or may be used in conjunction with the grain feeding mechanism or conveying mechanism whereby the grain quality can be measured as if it is flowing into the elevator.

While the above description has been directed to grain measurement, it will be appreciated that the invention can be used in other environments, and it will be understood that it is capable of further modifications and this application is intended to cover any modifications, uses or adaptations of the invention following in general the principles of the invention and including such departures from the present disclosure as come within known or customary practice in the art to which the invention pertains, and as may be applied to the essential features hereinbefore set forth and as fall within the scope of the invention or limits of the appended claims.

I claim:
1. A moisture measuring apparatus comprising:
   a. a probe for insertion into material to be measured, having a housing of dielectric material;
   b. means for generating a divergent electrostatic field substantially symmetrical about the probe housing and having a major portion thereof extending externally of the housing, said means including a pair of capacitance electrodes disposed within said probe physically isolated by said housing from the material to be measured,
   c. a frequency generating circuit including said electrodes, said frequency generating circuit providing an output signal having a frequency dependent upon the capacitance between said electrodes, and
   d. readout means connected to receive said output signal.
2. The apparatus of claim 1 including a temperature sensing element in contact with the material to be measured and being connected in said frequency generating circuit, the output frequency of said frequency generating circuit also being dependent upon the temperature of the material to be tested.
3. The apparatus of claim 2 including means for calibrating said frequency generating circuit for variance in temperature.
4. The apparatus of claim 1 wherein said frequency generating circuit includes a function generator therein.
5. The apparatus of claim 4 including means for providing a regulated DC voltage supply to said function generator including a DC power source connected to said function generator, and a zener diode and a second diode being series connected across said power source.
6. The apparatus of claim 1 including a shielded cable between said frequency generating circuit and said readout means.
7. The apparatus of claim 1 including means for remotely transmitting the output signal from said frequency generating circuit to said readout means.
8. The apparatus of claim 1 wherein said readout means includes a phase locked loop connected to receive the output signal from said frequency generating circuit.
9. The apparatus of claim 8 including an operational amplifier connected to said phase locked loop; means for adjusting the gain of said operational amplifier including a bank of resistors, the appropriate resistor being selected depending upon the material to be measured.
10. The apparatus of claim 9 including a means for indicating the voltage output connected to the output of said operational amplifier, said output voltage being in direct relationship to the dielectric constant of the material adjacent the probe.
11. The apparatus of claim 1 wherein the probe housing is elongated and of circular cross section, and said electrodes are cylindrical and longitudinally displaced within the probe housing.

* * * * *